United States Patent
Dutheuil

(10) Patent No.: US 12,054,457 B2
(45) Date of Patent: Aug. 6, 2024

(54) POLYMORPHS OF (2S,5R)-5-(2-CHLOROPHENYL)-1-(2'-METHOXY-[1,1'-BIPHENYL]-4-CARBONYL)PYRROLIDINE-2-CARBOXYLIC ACID AND PREPARATION PROCESSES THEREOF

(71) Applicant: EPICS THERAPEUTICS, Gosselies (BE)

(72) Inventor: Guillaume Dutheuil, Gosselies (BE)

(73) Assignee: EPICS THERAPEUTICS, Gosselies (BE)

( * ) Notice: Subject to any disclaimer, the term of this patent is extended or adjusted under 35 U.S.C. 154(b) by 0 days.

(21) Appl. No.: 18/484,653

(22) Filed: Oct. 11, 2023

(65) Prior Publication Data

US 2024/0132447 A1   Apr. 25, 2024

Related U.S. Application Data

(60) Provisional application No. 63/414,991, filed on Oct. 11, 2022.

(30) Foreign Application Priority Data

Oct. 11, 2022 (EP) .................................. 22200921.9

(51) Int. Cl.
C07D 207/16 (2006.01)

(52) U.S. Cl.
CPC ........ *C07D 207/16* (2013.01); *C07B 2200/13* (2013.01)

(58) Field of Classification Search
CPC ................. C07D 207/16; C07B 2200/13
See application file for complete search history.

(56) References Cited

FOREIGN PATENT DOCUMENTS

| WO | 2011073376 A1 | 6/2011 |
| WO | 2015078949 A1 | 6/2015 |
| WO | 2021250174 A1 | 12/2021 |

OTHER PUBLICATIONS

Hansen, J Med Chem, 2018, 61, 9534-9550. (Year: 2018).*
Bauer, "Pharmaceutical solids—The Amorphous Phase", Journal of Validation Technology, 2009, vol. 15, No. 3, pp. 63-68.
Newman et al., "Characterization of the "Hygroscopic" Properties of Active Pharmaceutical Ingredients", Journal of Pharmaceutical Sciences, Mar. 2008, vol. 97, No. 3, pp. 1047-1059.
Antunes et al., "Microbiota-derived acetate protects against respiratory syncytial virus infection through a GPR43-type 1 interferon response"; Nature Communications, 2019, 10:3273; 17 pages https://doi.org/10.1038/s41467-019-11152-6.
Fachi et al., "Acetate coordinates neutrophil and ILC3 responses against *C. difficile* through FFAR2"; Journal Experimental Medicine; 2019; 29 pages https://doi.org/10.1084/jem.20190489.
Miljkovic et al., "ILC3, a Central Innate Immune Component of the Gut-Brain Axis in Multiple Sclerosis"; Frontiers in Immunology; Apr. 12, 2021; vol. 12, Article 657622; 12 pages.
Razazan et al., "Activation of Microbiota Sensing—Free Fatty Acid Receptor 2 Signaling Ameliorates Amyloid-β Induced Neurotoxicity by Modulating Proteolysis-Senescence Axis"; Frontiers in Immunology; Oct. 5, 2021; vol. 13, Article 735933; 13 pages.
Sencio et al., "Gut Dysbiosis during Influenza Contributes to Pulmonary Pneumococcal Superinfection through Altered Short-Chain Fatty Acid Production"; Cell Reports 30, 2934-2947; Mar. 3, 2020; 21 pages.
Zhang et al., "GPR43 regulation of mitochondrial damage to alleviate inflammatory reaction in sepsis"; Aging 2021, vol. 13, No. 18; 23 pages.

* cited by examiner

*Primary Examiner* — D Margaret M Seaman
(74) *Attorney, Agent, or Firm* — Maier & Maier, PLLC

(57) ABSTRACT

Crystalline form I and form II of (2S,5R)-5-(2-chlorophenyl)-1-(2'-methoxy-[1,1'-biphenyl]-4-carbonyl)pyrrolidine-2-carboxylic acid and preparation processes thereof. Also, a method for treating an inflammatory disease in a patient in need thereof, which includes administering to the patient a therapeutically effective amount of the crystalline form I or the crystalline form II of (2S,5R)-5-(2-chlorophenyl)-1-(2'-methoxy-[1,1'-biphenyl]-4-carbonyl) pyrrolidine-2-carboxylic acid.

15 Claims, 8 Drawing Sheets

POLYMORPHS OF (2S,5R)-5-(2-CHLOROPHENYL)-1-(2'-METHOXY-[1,1'-BIPHENYL]-4-CARBONYL) PYRROLIDINE-2-CARBOXYLIC ACID AND PREPARATION PROCESSES THEREOF

FIELD

The present invention relates to crystalline forms of (2S,5R)-5-(2-chlorophenyl)-1-(2'-methoxy-[1,1'-biphenyl]-4-carbonyl)pyrrolidine-2-carboxylic acid, namely crystalline form I and crystalline form II. The invention also provides preparation processes of crystalline forms I and II. The crystalline forms I and II are useful for the treatment of diseases associated with or mediated by free fatty acid receptor 2 (FFAR2) also named GPR43 receptor.

BACKGROUND

The pyrrolidine carboxylic acid derivatives disclosed in WO2011/073376 are FFAR2 agonists which are useful for the treatment of inflammatory diseases, as reported in WO2015/078949. Especially, it was evidenced that (2S,5R)-5-(2-chlorophenyl)-1-(2'-methoxy-[1,1'-biphenyl]-4-carbonyl)pyrrolidine-2-carboxylic acid, hereafter referred to as compound (1), is of particular interest for the treatment of inflammatory diseases. A scalable process of manufacturing of compound (1) was reported in WO2021/250174, as well as its corresponding sodium salt (compound (1.Na)).

Compound (1)

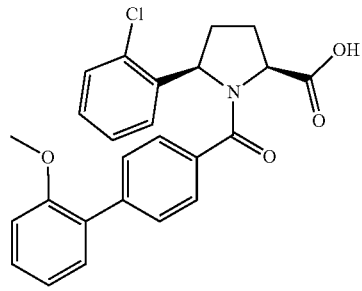

In all above references, compound (1), as well as its sodium salt (1.Na), were obtained under amorphous form. However, the amorphous forms of compounds (1) and (1.Na) present the major drawback to be very hygroscopic, leading to several problems for the manufacturing of the compound, its handling, storage, and use in solid formulation.

Besides, for active ingredients to be used in pharmaceutical preparations (i.e. active pharmaceutical ingredient (API)), the amount of residual solvents in the drug substance needs to be as low as possible in order to encounter residual solvent requirements of the Pharmacopeias. Indeed, the presence of traces of an organic solvent may be harmful, hence, the use of solvates of an API is discouraged in pharmaceuticals. Moreover, even hydrates of the API, have preferably to be avoided, since they have tendency to be hygroscopic and may require more controls for manufacturing, storage and in-use for the formulation. The hydrate normally has lower aqueous solubility than the anhydrate rendering absorbable dose harder to achieve.

There was thus a need to provide a non-hygroscopic form of compound (1), in a non-solvated-form.

Investigating polymorphism during drug development is a common practice. However, the formation of polymorphs, their compositions (i.e. the molecule alone or under the form of a salt and/or solvate) and their properties are unforeseeable.

Different crystalline forms of a same compound can have different physical properties such as different packing, thermodynamic, spectroscopic, kinetic, surface and mechanical properties. This can lead to differences in terms of ease of processing, stability, possibilities of formulation as dosage form, dissolution rate and thus bioavailability. Although general approaches to crystalline form screening of API are known, it is well established that the prediction whether a given compound will exhibit polymorphism is not possible. Furthermore, the prediction of the properties of the crystalline forms, if any, and how they will differ from each other, remains even more elusive.

During the investigations conducted by the Applicant, several polymorphic forms of compound (1) were identified, i.e. at least 10 forms, being unfortunately mostly solvated forms, i.e. polymorphic forms of compound (1) comprising one or more molecules of solvent. Among all the identified polymorphic forms, only crystalline forms I and II were evidenced to be non-solvated and non-hygroscopic. Moreover, crystalline form I was evidenced to be particularly stable, especially compared to form II.

The present invention thus provides crystalline forms I and II of compound (1), which are anhydrous and non-solvated polymorphs, being non-hygroscopic. Advantageously, form I is particularly stable, compared to form II.

SUMMARY

This invention thus relates to a crystalline form of (2S,5R)-5-(2-chlorophenyl)-1-(2'-methoxy-[1,1'-biphenyl]-4-carbonyl)pyrrolidine-2-carboxylic acid, of form I or form II, wherein:
form I is characterized by an XRPD pattern comprising peaks at 2θ angle values of 13.5°, 14.0°, 14.8°, 16.0° and 18.0°; and
form II is characterized by an XRPD pattern comprising peaks at 2θ angle values of 10.8°, 12.10, 12.4° and 22.3°.

In one embodiment, form I has an XRPD pattern comprising peaks at 2θ angle values of 7.20, 12.80, 13.50, 14.00, 14.50, 14.80, 16.00, 16.70, 17.40, 18.00, 18.90, 19.90, 20.40, and 23.2°. In one embodiment, form I has an XRPD pattern substantially as shown in FIG. 1.

In one embodiment, form I has a DSC thermogram which exhibits an endotherm with a peak temperature of about 183° C. and an onset temperature of about 180° C.

In one embodiment, form I has unit cell parameters equal to:
Cell dimensions:
a=11.51(2) A
b=13.95(3) A
c=15.14(3) A
α, β, γ=90°
Space group: $P2_12_12_1$
Molecules per unit cell: 4
Unit cell volume: 2430.9 (8) Å$^3$
Density (calculated): 1.19 g/cm$^3$.

In one embodiment, form II has an XRPD pattern comprising peaks at 2θ angle values of 10.8°, 12.10, 12.4°, 15.3°, 16.2°, 18.5°, 19.5°, 20.7°, 21.5° and 22.3°. In one embodiment, form II has an XRPD pattern substantially as shown in FIG. 5.

In one embodiment, form II has a DSC thermogram which exhibits a first endotherm, with a peak temperature of about 110° C. and an onset at about 100° C., an exotherm with a peak temperature of about 149° C. and an onset at about 134° C., and a second an endotherm with a peak temperature of about 181° C. and an onset at about 179° C.

The invention also provides a process for preparing the crystalline form I comprising:
1) dissolving (2S,5R)-5-(2-chlorophenyl)-1-(2'-methoxy-[1,1'-biphenyl]-4-carbonyl)pyrrolidine-2-carboxylic acid in an ethanol/water mixture, wherein the ethanol/water ratio is ranging from 100/0 to 5/95, at a temperature up to 80° C.;
2) if relevant, adding water in order to reach an ethanol/water ratio ranging from 95/5 to 5/95, wherein water is preferably heated at the same temperature as ethanol used in step 1); and
3) cooling the mixture, preferably to a temperature ranging from 0° C. to 10° C., and maintaining this temperature during a period of time suitable to recover crystalline form I.

The invention further provides process for preparing the crystalline form II comprising:
1) dissolving (2S,5R)-5-(2-chlorophenyl)-1-(2'-methoxy-[1,1'-biphenyl]-4-carbonyl)pyrrolidine-2-carboxylic acid in acetonitrile, at a temperature up to 80° C.; and
2) cooling the mixture of step 1), preferably to room temperature, and maintaining this temperature during a period of time suitable to recover crystalline form II.

The invention also provides a pharmaceutical composition comprising a crystalline form according to the invention, and at least one pharmaceutically acceptable carrier.

The invention also relates to a crystalline form according to the invention, for use as a medicament.

The invention further relates to a crystalline form according to the invention, for use in the treatment of an inflammatory disease, wherein the inflammatory disease is selected from rheumatoid arthritis; inflammatory bowel disease (IBD), including but not limited to Crohn's disease, and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); immune-mediated colitis (IMC) (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute myelogenous leukemia, chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; autoimmune brain diseases, such as encephalitis, and encephalomyelitis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1), such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease.

In one embodiment, the inflammatory disease is selected from rheumatoid arthritis; inflammatory bowel disease (IBD), Crohn's disease, ulcerative colitis; colitis; collagenous colitis; lymphocytic colitis; immune-related enterocolitis; immune-mediated colitis (IMC); pouchitis; Celiac disease; irritable bowel syndrome; gut dysbiosis; Pagets disease; osteoporosis; multiple myeloma; uveitis; acute myelogenous leukemia, chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis; asthma; muscle degeneration; cachexia; Reiter's syndrome; type I diabetes; bone resorption disease; graft vs. host reaction; ischemia reperfusion injury; brain trauma; multiple sclerosis; autoimmune brain diseases, encephalitis, encephalomyelitis; cerebral malaria; sepsis; septic shock; toxic shock syndrome; endotoxic shock; gram negative sepsis; fever and myalgias due to infection; pyrosis; inflammatory conditions consequent to the release of anorectic gut hormones; microbiome-related neurological and mood disorders, and neurodegenerative diseases characterized by neuroinflammation.

In one embodiment, the inflammatory disease is selected from inflammatory bowel disease (IBD), Crohn's disease, ulcerative colitis, colitis, collagenous colitis, lymphocytic colitis, immune-related enterocolitis (including as an adverse event in response to cancer therapy with checkpoint inhibitors such as inhibitors of CTLA-4, PD-1, PD-L1), immune-mediated colitis (IMC) (including as an adverse event in response to cancer therapy with checkpoint inhibitors such as inhibitors of CTLA-4, PD-1, PD-L1), pouchitis, Celiac disease, irritable bowel syndrome, gut dysbiosis, type 1 diabetes, multiple sclerosis, autoimmune brain diseases such as encephalitis and encephalomyelitis. In one embodiment, the inflammatory disease is selected from inflammatory bowel disease (IBD), Crohn's disease, ulcerative colitis, colitis, collagenous colitis, lymphocytic colitis, immune-related enterocolitis, immune-mediated colitis (IMC), pouchitis, Celiac disease, irritable bowel syndrome, gut dysbiosis, type 1 diabetes, multiple sclerosis, autoimmune brain diseases, encephalitis, and encephalomyelitis. In one embodiment, the immune-related enterocolitis is an immune-related enterocolitis occurring as an adverse event in response to cancer therapy with checkpoint inhibitors, preferably the checkpoint inhibitors are inhibitors of CTLA-4, PD-1, and/or PD-L1. In one embodiment, the immune-mediated colitis (IMC) is an immune-mediated colitis occurring as an adverse event in response to cancer therapy with checkpoint inhibitors, preferably the checkpoint inhibitors are inhibitors of CTLA-4, PD-1, and/or PD-L1.

The invention further to relates to a crystalline form according to the invention, for use in the treatment of an inflammatory disease, wherein the inflammatory disease is preferably selected from inflammatory bowel disease (IBD), colitis, collagenous colitis, lymphocytic colitis, immune-related enterocolitis, pouchitis, Celiac disease, irritable bowel syndrome, and gut dysbiosis.

The invention further to relates to a crystalline form according to the invention, for use in the treatment of cancer, wherein the cancer is preferably selected from lung cancer, non-small cell lung cancer, small cell lung cancer, breast cancer, prostate cancer, ovarian cancer, endometrial cancer, vaginal cancer, testicular cancer, cervical cancer, bladder cancer, head and neck cancer, kidney cancer, renal cell carcinoma, esophageal cancer, pancreatic cancer, brain cancer, thyroid cancer, gastrointestinal cancer, colorectal cancer, stomach cancer, colon cancer, liver cancer, leukemia, lymphoma, skin cancer, melanoma, multiple myeloma, glioma, glioblastoma, mesothelioma, retinoblastoma, sarcoma, Ewing's sarcoma, Kaposi's sarcoma, osteosarcoma, fibrosarcoma, bone cancer, and cardiac cancer.

DETAILED DESCRIPTION

Figure 1:
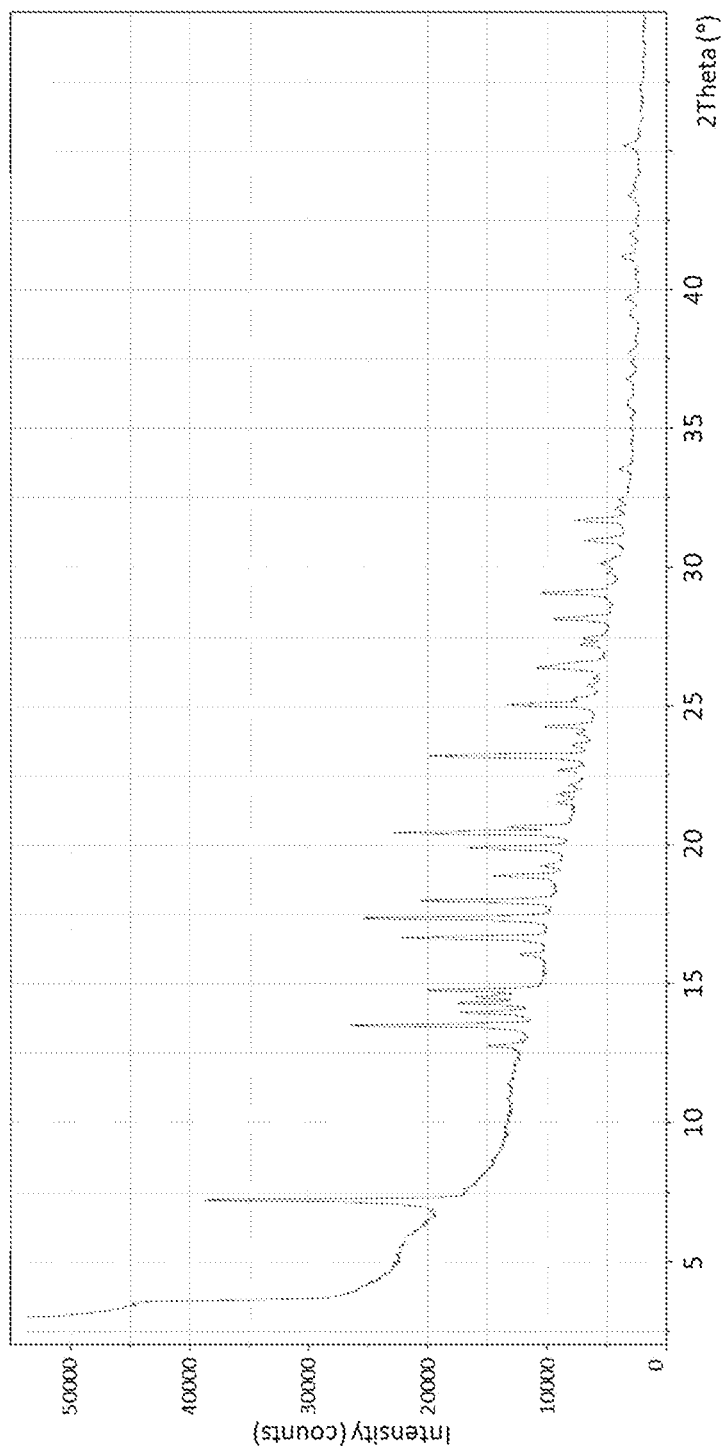
FIG. 1 is an X-ray powder diffraction (XRPD) pattern of the crystalline form I.

In the present invention, the following terms have the following meanings:

"About", preceding a figure, means plus or less 10% of the value of said figure, preferably plus or less 5% of the value of said figure.

"Administration", or a variant thereof (e.g. "administering"), means providing the active agent or active ingredient, alone or as part of a pharmaceutically acceptable composition, to the patient in whom/which the condition, symptom, or disease is to be treated or prevented.

"Amorphous", or "non-crystalline", when used to describe a substance, refers to a solid state of said substance, and means that the substance arranges in an indefinite geometry, i.e. in the form of irregular arrays, by contrast to a crystalline form. The amorphous state of a substance can be determined for example by X-ray diffraction.

"Crystalline", when used to describe a substance, refers to a solid state of said substance, and means that the substance arranges in a definite geometry, i.e. in the form of regular arrays. The crystalline state of a substance can be determined for example by X-ray diffraction.

"Crystalline form", "polymorphic form" or "polymorph" are herein used indifferently, with the same meaning, unless otherwise stated. When used to describe a substance, "crystalline form", "polymorphic form" or "polymorph" refer to a tridimensional structure in which the substance is organized in the solid state, by contrast to its amorphous form. A substance can have several crystalline forms. Each crystalline form of a substance exhibits different physical properties.

The terms "crystalline form", "polymorphic form" or "polymorph" can refer either to a crystalline solid state of the substance only, or to a crystalline solid state of the substance under the form of a salt and/or solvate thereof.

"Non-solvated crystalline form", refers to a crystalline form of a substance which is essentially free of solvent (e.g. less than 1% by weight of solvent based on the total weight of substance), meaning that there is substantially no molecules of solvent inside the crystal assembly (stoichiometrically or non-stoichiometrically). An "anhydrous form" is a specific case of a "non-solvated form", wherein the solvent is water.

"Solvated crystalline form", refers to a crystalline form of a substance which comprises molecules of solvent, under a stoichiometrically or non-stoichiometrically ratio with regard to the substance.

"Patient" refers to a mammal, more preferably a human, who/which is awaiting the receipt of, or is receiving medical care or is/will be the object of a medical procedure.

"Pharmaceutically acceptable" refers to the ingredients of a pharmaceutical composition which are compatible with each other and not deleterious to the subject to which it is administered.

"Pharmaceutically acceptable carrier" refers to a substance that does not produce an adverse, allergic or other untoward reaction when administered to an animal, preferably a human. It includes any and all inactive substance such as for example solvents, cosolvents, antioxidants, surfactants, stabilizing agents, emulsifying agents, buffering agents, pH modifying agents, preserving agents (or preservating agents), antibacterial and antifungal agents, isotonifiers, granulating agents or binders, lubricants, disintegrants, glidants, diluents or fillers, adsorbents, dispersing agents, suspending agents, coating agents, bulking agents, gelatin (for soft and hard capsules), release agents, absorption delaying agents, sweetening agents, flavoring agents and the like. For human administration, preparations should meet sterility, pyrogenicity, general safety and purity standards as required by regulatory offices, such as, e.g., FDA Office or EMA.

"Therapeutically effective amount" refers to the amount or dose of active ingredient that is aimed at, without causing significant negative or adverse side effects to the subject, (1) delaying or preventing the onset of a disease in the subject; (2) reducing the severity or incidence of a disease; (3) slowing down or stopping the progression, aggravation, or deterioration of one or more symptoms of a disease, affecting the subject; (4) bringing about ameliorations of the symptoms of a disease, affecting the subject; or (5) curing a disease, affecting the subject. A therapeutically effective amount may be administered prior to the onset of a disease, for a prophylactic or preventive action. Alternatively, or additionally, a therapeutically effective amount may be administered after initiation of a disease, for a therapeutic action.

"Treating" or "treatment" as used herein, refer to a therapeutic treatment, to a prophylactic (or preventative) treatment, or to both a therapeutic treatment and a prophylactic (or preventative) treatment, wherein the object is to prevent, reduce, alleviate, and/or slow down (lessen) one or more of the symptoms of the targeted pathologic condition or disease, in a subject in need thereof. In one embodiment, "treating" or "treatment" refers to a therapeutic treatment. In another embodiment, "treating" or "treatment" refers to a prophylactic or preventive treatment. In yet another embodiment, "treating" or "treatment" refers to both a prophylactic (or preventative) treatment and a therapeutic treatment. In one embodiment, "treating" or "treatment" refers to the therapeutic treatment of one or more symptoms of a disease associated with or mediated by FFAR2.

"Subject" refers to a mammal, preferably a human. In one embodiment, the subject is diagnosed with a disease. In one embodiment, the subject is a patient, preferably a human patient, who/which is awaiting the receipt of, or is receiving, medical care or was/is/will be the subject of a medical procedure or is monitored for the development or progression of a disease. In one embodiment, the subject is a human patient who is treated and/or monitored for the development or progression of a disease. In one embodiment, the subject is a male. In another embodiment, the subject is a female. In one embodiment, the subject is an adult. In another embodiment, the subject is a child.

This invention thus relates to two polymorphs of (2S,5R)-5-(2-chlorophenyl)-1-(2'-methoxy-[1,1'-biphenyl]-4-carbonyl)pyrrolidine-2-carboxylic acid, which are non-solvated and non-hygroscopic. These two novel crystalline forms are referred to as "form I" and "form II" respectively.

Characterizations of the crystalline forms I and II of the invention are provided hereafter. Depending on the measurement conditions, equipment and other common variables known to one skilled in the art, crystalline forms I and II may display similar, yet non-identical, analytical characteristics within a reasonable range of error, compared to what is herein reported.

Crystalline Form I

In one embodiment, the invention thus relates to crystalline form I of (2S,5R)-5-(2-chlorophenyl)-1-(2'-methoxy-[1,1'-biphenyl]-4-carbonyl)pyrrolidine-2-carboxylic acid.

The crystalline form I is characterized by an X-ray powder diffraction (XRPD) pattern comprising peaks at 2θ angle values of 13.5°, 14.0°, 14.8°, 16.0° and 18.0°.

The 2θ angle values provided herein are for a measure at room temperature, in the conditions detailed in example 2. In one embodiment, the peaks of the XRPD pattern are measured using an X-ray wavelength of 1.5406 Å. In one embodiment, the range of error for the angle values provided is of ±0.2°, preferably of ±0.10.

In one embodiment, the crystalline form I has an XRPD pattern comprising peaks at 2θ angle values of 7.2°, 12.8°, 13.5°, 14.0°, 14.5°, 14.8°, 16.0°, 16.7°, 17.4°, 18.0°, 18.9°, 19.9°, 20.4°, and 23.2°.

In one embodiment, the crystalline form I has an XRPD pattern comprising peaks at 2θ angle values similar to those shown in Table 1.

TABLE 1

| XRPD pattern of crystalline form I, with relative intensity of the reflection peaks (2θ). | |
|---|---|
| Angle 2θ (°) | Relative intensity (%) |
| 7.2 | 100 |
| 12.8 | 14.2 |
| 13.5 | 70.0 |
| 14.0 | 26.9 |
| 14.5 | 24.3 |
| 14.8 | 44.8 |
| 16.0 | 10.4 |
| 16.7 | 54.4 |
| 17.4 | 74.4 |
| 18.0 | 51.0 |
| 18.9 | 25.0 |
| 19.9 | 38.5 |
| 20.4 | 67.0 |
| 20.6 | 24.1 |
| 23.2 | 61.6 |
| 24.3 | 18.6 |
| 25.1 | 33.6 |
| 26.4 | 25.5 |
| 28.2 | 22.5 |

TABLE 1-continued

| XRPD pattern of crystalline form I, with relative intensity of the reflection peaks (2θ). | |
|---|---|
| Angle 2θ (°) | Relative intensity (%) |
| 29.1 | 28.7 |
| 31.0 | 14.8 |
| 31.7 | 19.0 |

In one embodiment, the crystalline form I has an XRPD pattern substantially as shown in FIG. 1.

In one embodiment, the crystalline form I crystallizes in an orthorhombic cell structure, with the unit cell parameters equal to:

Cell dimensions:
  a=11.51(2) Å
  b=13.95(3) Å
  c=15.14(3) Å
  $\alpha, \beta, \gamma = 90°$ Space group: $P2_12_12_1$ Molecules per unit cell: 4

Unit cell volume: 2430.9 (8) Å$^3$

Density (calculated): 1.19 g/cm$^3$

In one embodiment, the crystalline form I has a differential scanning calorimetry (DSC) thermogram which exhibits an endotherm with a peak temperature of about 183° C. and an onset temperature of about 180° C.

Figure 2:
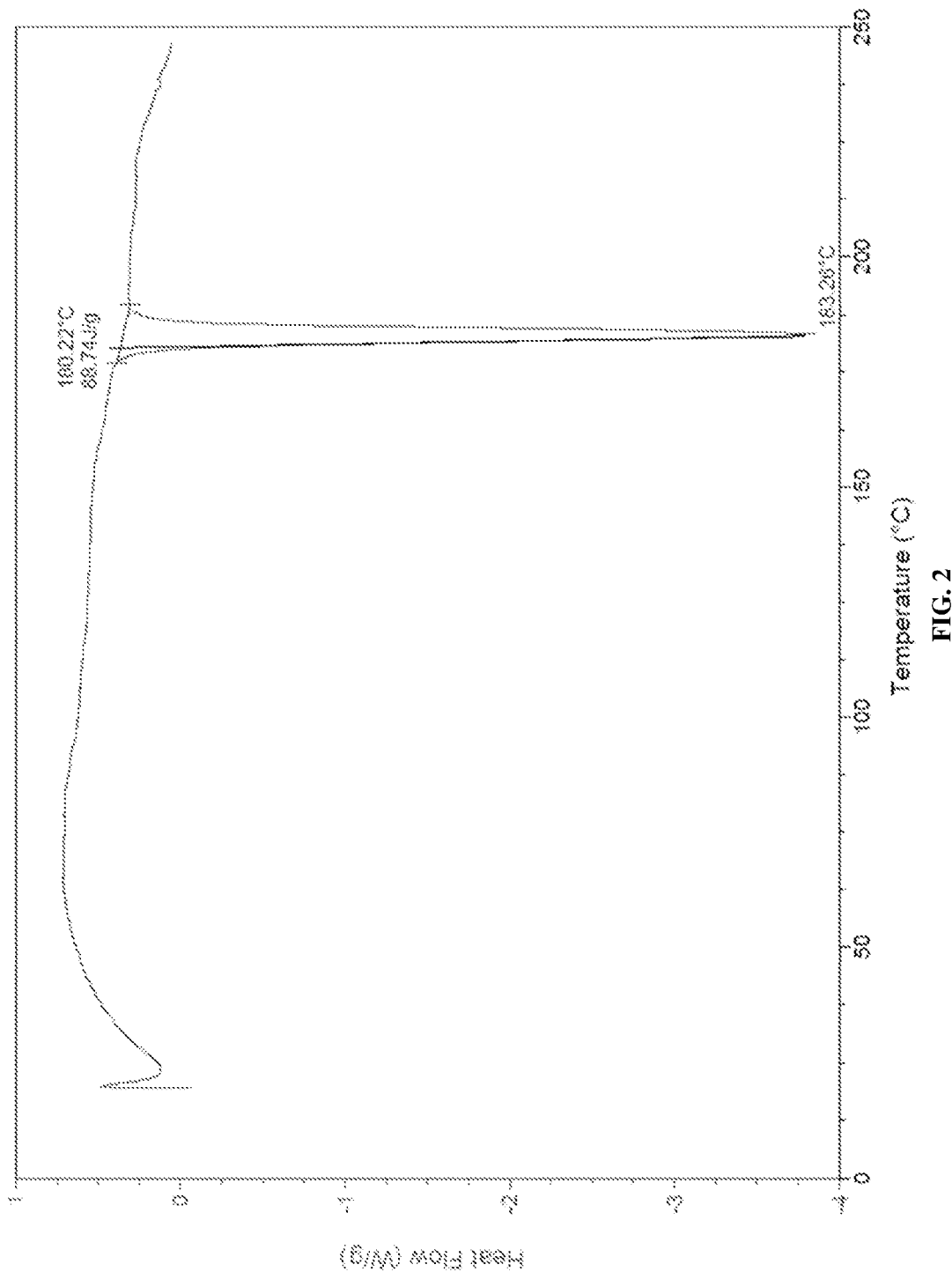
FIG. 2 is a differential scanning calorimetric (DSC) thermogram of the crystalline form I.

In one embodiment, the crystalline form I has a DSC thermogram substantially as shown in FIG. 2.

Figure 3:
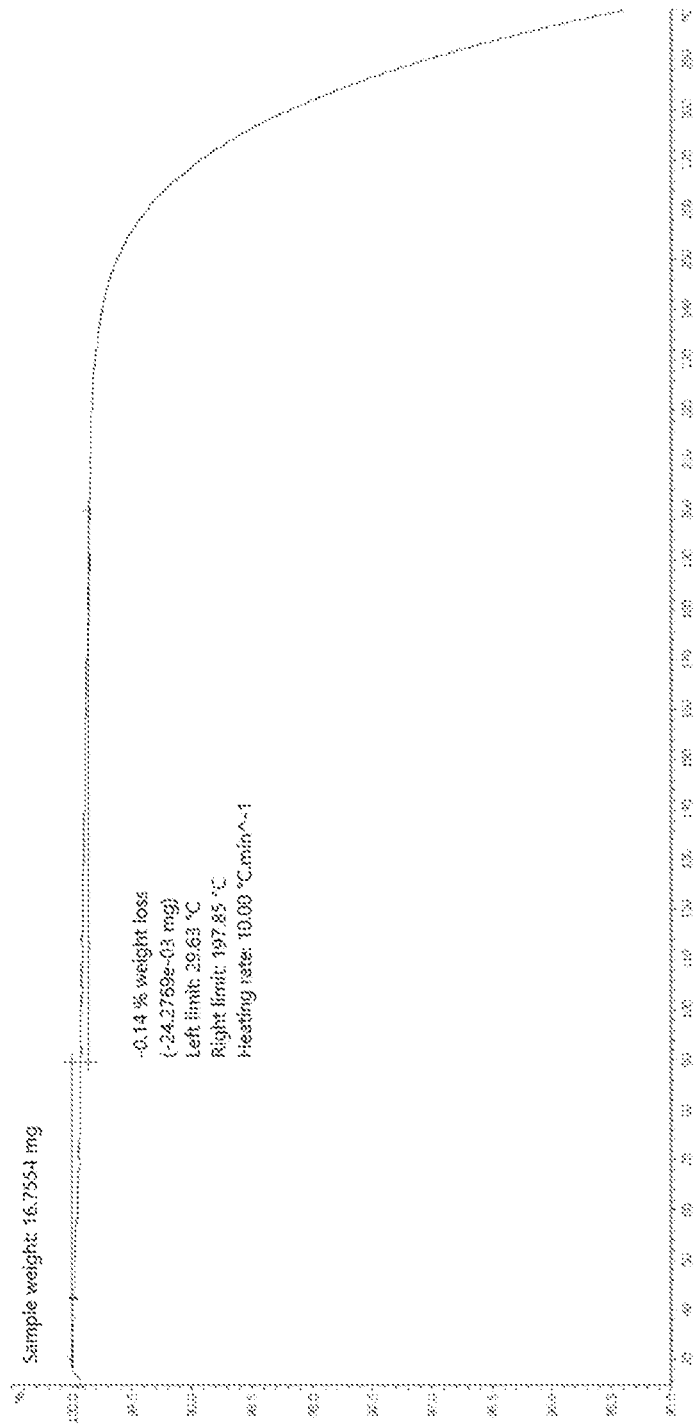
FIG. 3 is a thermal gravimetric analysis (TGA) thermogram of the crystalline form I.

In one embodiment, the crystalline form I has a thermogravity analysis (TGA) thermogram which exhibits no significant weight loss below 220° C., substantially as shown in FIG. 3. Above this temperature, the observed weight loss is likely due to the evaporation and/or degradation.

It was evidenced that crystalline form I is advantageously non-hygroscopic.

Figure 4:
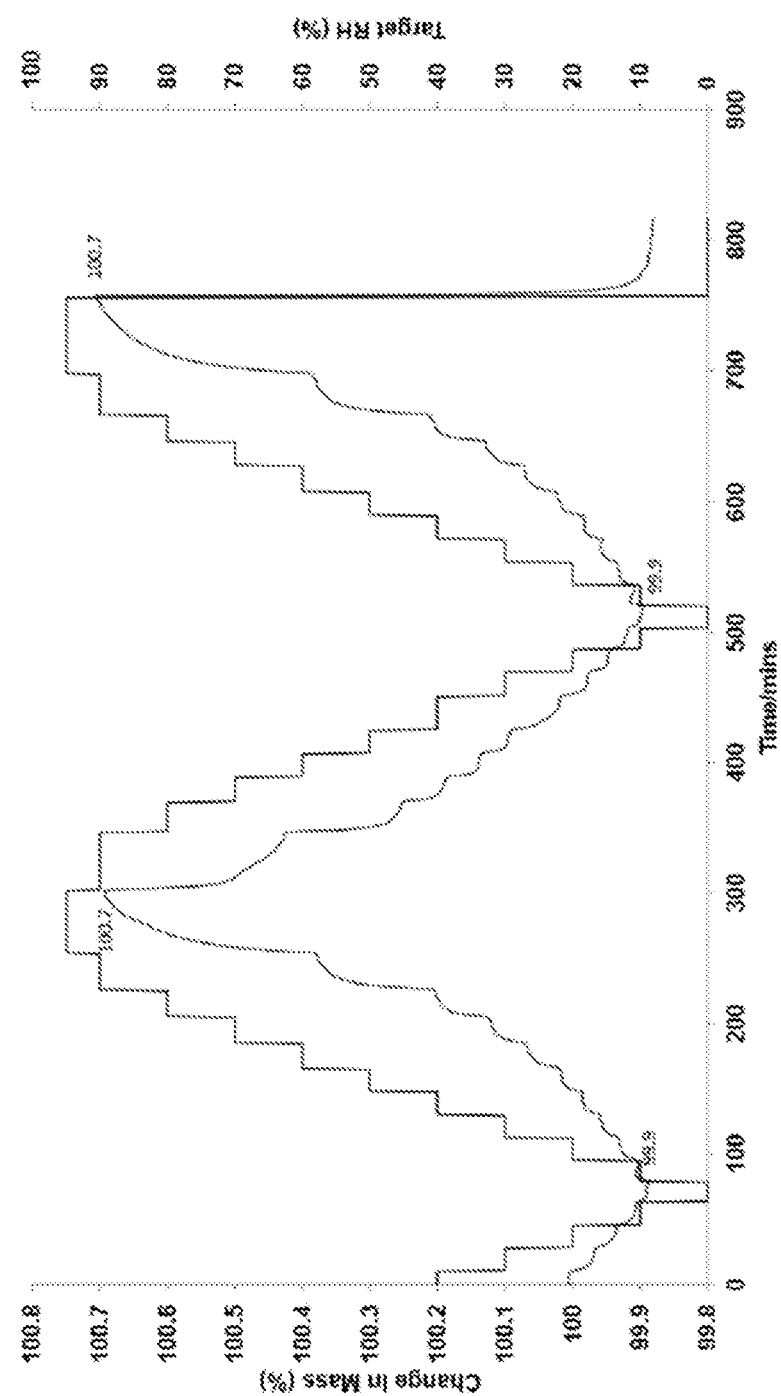
FIG. 4 is a dynamic vapor sorption (DVS) isotherm plot of the crystalline form I.

Especially, water sorption/desorption profiles were established for crystalline form I, as reported on the dynamic vapor sorption (DVS) isotherm plot of FIG. 4 and as detailed in example 6.

It was also evidenced that crystalline form I is thermodynamically stable. Especially, form I is thermodynamically stable for at least 6 months, preferably at least 12 months, more preferably at least 18 months.

Crystalline Form II

In one embodiment, the inventive also relates to crystalline form II of (2S,5R)-5-(2-chlorophenyl)-1-(2'-methoxy-[1,1'-biphenyl]-4-carbonyl)pyrrolidine-2-carboxylic acid.

The crystalline form II is characterized by an XRPD pattern comprising peaks at 2θ angle values of 10.8°, 12.10, 12.4° and 22.3°.

The 2θ angle values provided herein are for a measure at room temperature, in the conditions detailed in example 2. In one embodiment, the peaks of the XRPD pattern are measured using an X-ray wavelength of 1.5406 Å. In one embodiment, the range of error for the angle values provided is of ±0.2°, preferably of ±0.10.

In one embodiment, the crystalline form II has an XRPD pattern comprising peaks at 2θ angle values of 10.8°, 12.1°, 12.4°, 15.3°, 16.2°, 18.5°, 19.5°, 20.7°, 21.5° and 22.3°.

In one embodiment, the crystalline form II has an XRPD pattern comprising peaks at 2θ angle values similar to those shown in Table 2.

TABLE 2

XRPD pattern of crystalline form II, with relative
intensity of the reflection peaks (2θ).

| Angle 2θ (°) | Relative intensity (%) |
| --- | --- |
| 10.4 | 19.3 |
| 10.8 | 100 |
| 12.1 | 68.6 |
| 12.4 | 29.9 |
| 15.3 | 11.8 |
| 16.2 | 21.8 |
| 18.5 | 17.7 |
| 18.7 | 13.6 |
| 19.5 | 14.5 |
| 19.7 | 11.3 |
| 20.7 | 24.7 |
| 21.5 | 16.7 |
| 22.3 | 47.5 |
| 24.4 | 12.4 |
| 24.8 | 13.1 |

Figure 5:
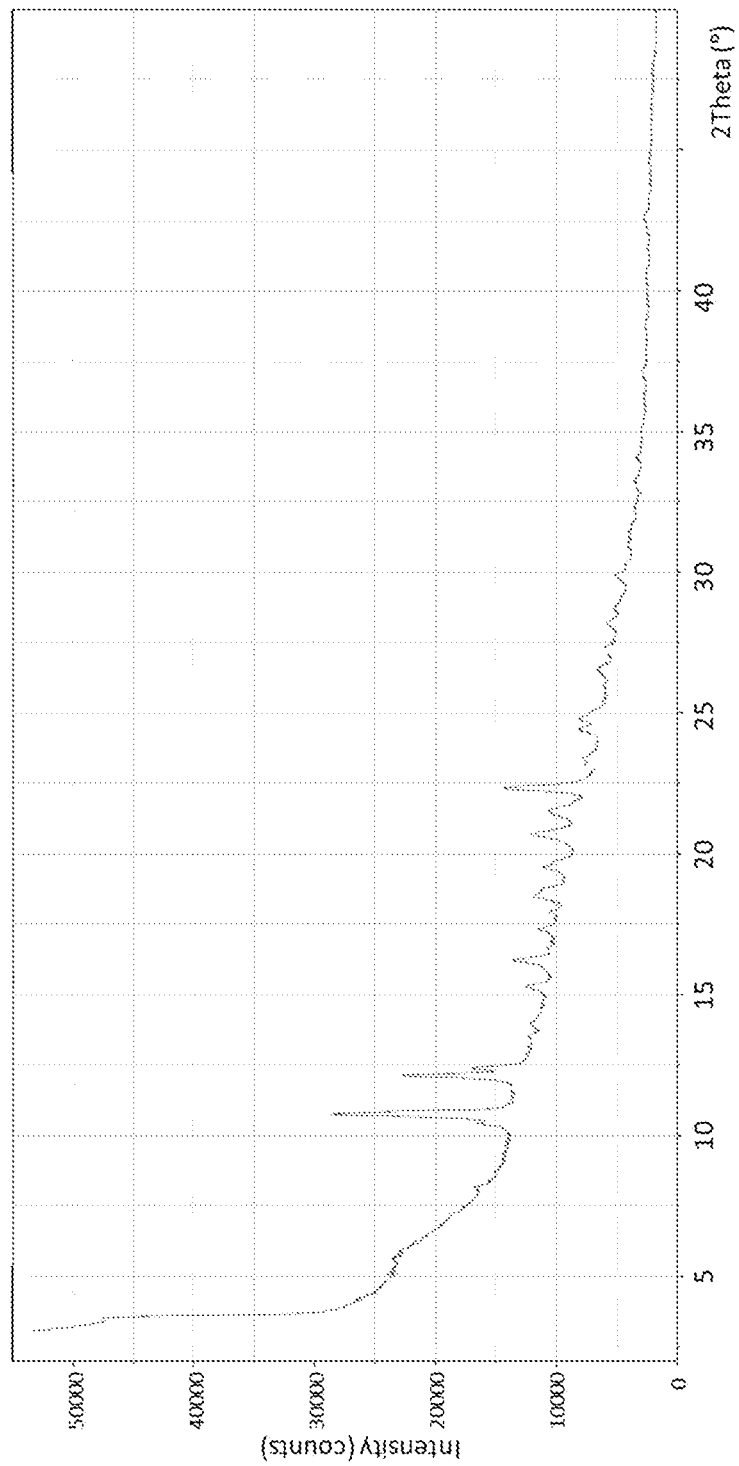
FIG. 5 is an XRPD pattern of the crystalline form II.

In one embodiment, the crystalline form II has an XRPD pattern substantially as shown in FIG. 5.

In one embodiment, the crystalline form II has a DSC thermogram which exhibits a first endotherm, with a peak temperature of about 110° C. and an onset at about 100° C., an exotherm with a peak temperature of about 149° C. and an onset at about 134° C., and a second an endotherm with a peak temperature of about 181° C. and an onset at about 179° C.

Figure 6:
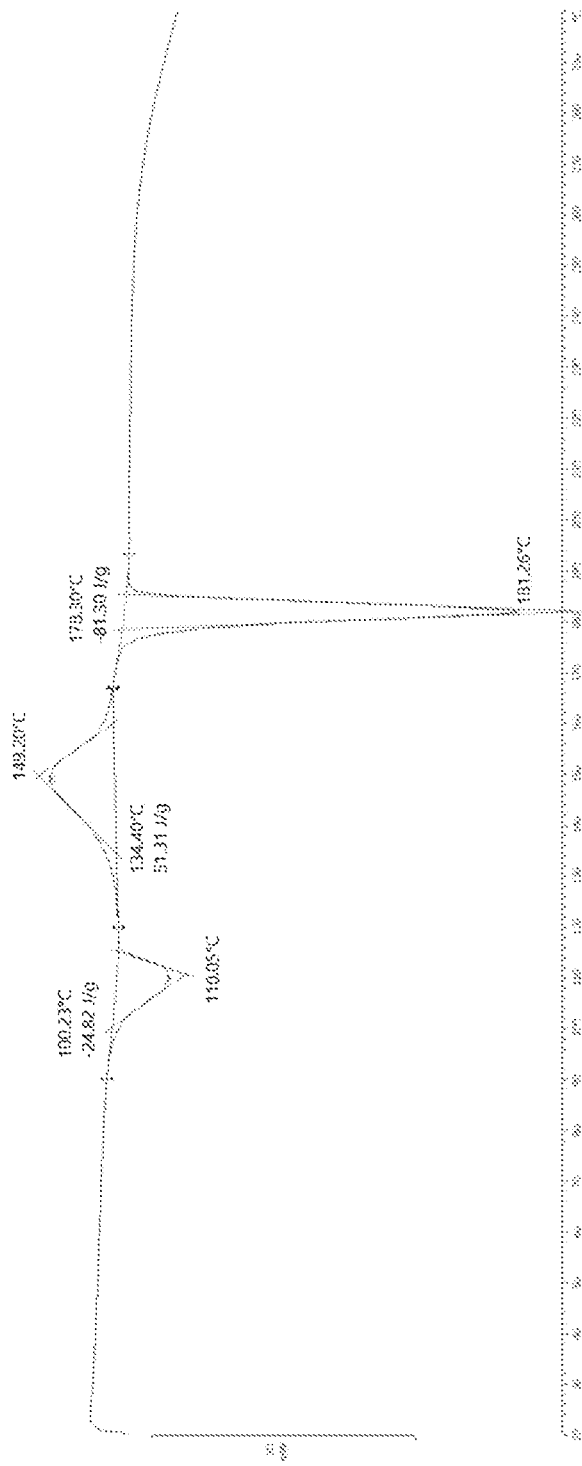
FIG. 6 is a DSC thermogram of the crystalline form II.

In one embodiment, the crystalline form II has a DSC thermogram substantially as shown in FIG. 6.

Figure 7:
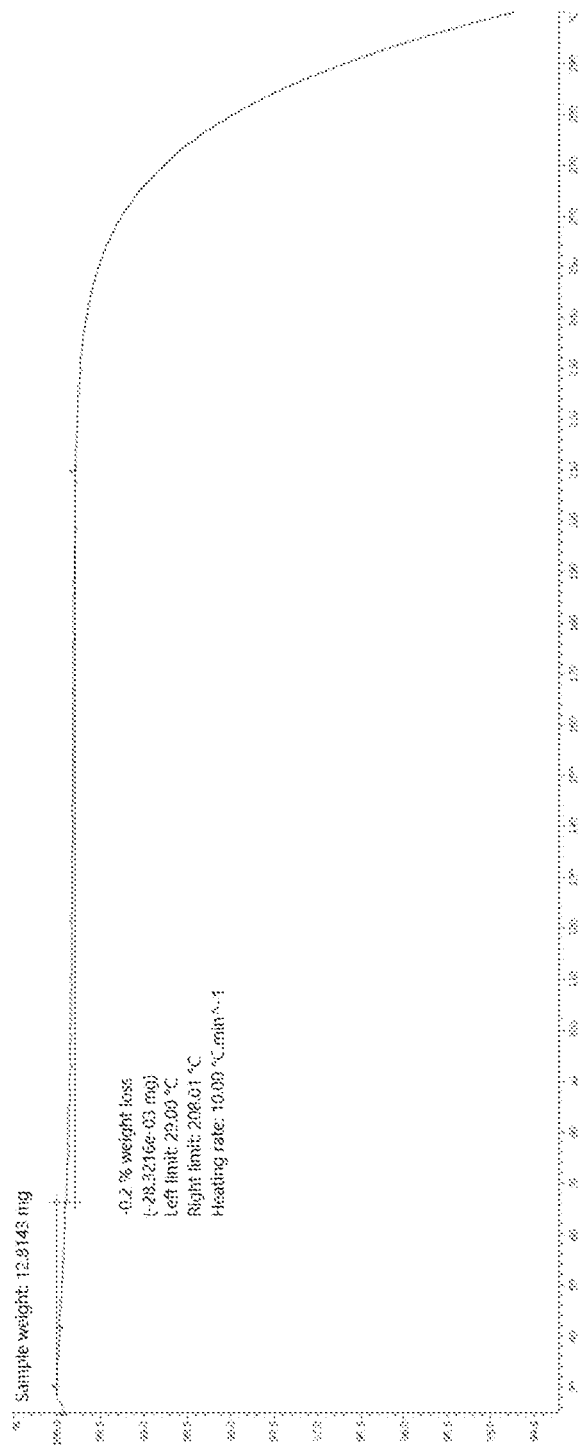
FIG. 7 is a TGA thermogram of the crystalline form II.

In one embodiment, the crystalline form II has a TGA thermogram which exhibits no significant weight loss below 220° C., substantially as shown in FIG. 7.

It was evidenced that crystalline form II is advantageously non-hygroscopic. Especially, water sorption/desorption profiles were established for crystalline form II, as reported on the DVS isotherm plot of FIG. 8 and as detailed in example 6.

Process of Manufacturing

The crystalline forms I and II can be prepared by various methods available to one skilled in the art, including by the methods described hereafter and in the examples.

The invention thus relates to a process for preparing the crystalline form I of the invention, comprising crystallizing (2S,5R)-5-(2-chlorophenyl)-1-(2'-methoxy-[1,1'-biphenyl]-4-carbonyl)pyrrolidine-2-carboxylic acid from an ethanol/water mixture.

In one embodiment the process for preparing the crystalline form I comprises crystallizing (2S,5R)-5-(2-chlorophenyl)-1-(2'-methoxy-[1,1'-biphenyl]-4-carbonyl)pyrrolidine-2-carboxylic acid (compound (1)) from an ethanol/water mixture in a ratio ranging from 95/5 to 5/95, at a temperature up to 80° C., in a volume-to-weight ratio preferably ranging from 1 to 20 volume of solvent mixture to compound (1) weight.

By "volume-to-weight ratio" it is referred to the ratio of the volume of solvent (e.g. in mL or L) to the weight of compound (e.g. in g or kg respectively), involved in the process.

In one embodiment, the process for preparing the crystalline form I comprises the following steps:
1) dissolving (2S,5R)-5-(2-chlorophenyl)-1-(2'-methoxy-[1,1'-biphenyl]-4-carbonyl)pyrrolidine-2-carboxylic acid (compound (1)) in an ethanol/water mixture, wherein the ethanol/water ratio is ranging from 100/0 to 5/95, at a temperature up to 80° C., preferably ranging from 40° C. to 60° C., more preferably from 45° C. to 55° C.;
2) if relevant, adding water in order to reach an ethanol/water ratio ranging from 95/5 to 5/95, wherein water is preferably heated at the same temperature as ethanol used in step 1); and
3) cooling the mixture, preferably to a temperature ranging from 0° C. to 10° C., more preferably from 3° C. to 5° C., and maintaining this temperature during a period of time suitable to recover crystalline form I.

In one embodiment, in step 1), compound (1) is directly dissolved in an ethanol/water mixture having the ethanol/water ratio targeted for crystallization, i.e. ranging from 95/5 to 5/95. In such case, step 2) is absent.

In another embodiment, in step 1), compound (1) is dissolved in an ethanol/water mixture comprising more ethanol than the ethanol/water ratio targeted for crystallization. In such case, water is added pursuant to step 2) in order to reach the ethanol/water ratio targeted for crystallization, ranging from 95/5 to 5/95. In a specific embodiment, in step 1), compound (1) is dissolved in ethanol and in step 2), water is added to reach an ethanol/water ratio ranging from 95/5 to 5/95. In one embodiment, when compound (1) is dissolved in ethanol in step 1), it can be filtered and rinsed with a small volume of ethanol heated at the working temperature, before that water is added pursuant to step 2) to the resulting ethanol filtrate.

In one embodiment, the ethanol/water ratio (in volume) used for crystallizing compound (1) to form I is ranging from 95/5 to 5/95, preferably from 95/5 to 50/50, preferably from 95/5 to 65/35. In one embodiment the ethanol/water ratio used for crystallizing compound (1) to form I is of 95/5 in volume. In another embodiment the ethanol/water ratio used for crystallizing compound (1) to form I is of 75/25 in volume. In another embodiment the ethanol/water ratio used for crystallizing compound (1) to form I is of 70/30 in volume.

In one embodiment, the volume-to-weight ratio of ethanol/water mixture to compound (1) used for crystallizing compound (1) to form I is ranging from 1 to 20, preferably from 3 to 7. In one embodiment, the volume-to-weight ratio of ethanol/water mixture to compound (1) used for crystallizing compound (1) to form I is equal to 3. In another embodiment, the volume-to-weight ratio of ethanol/water mixture to compound (1) used for crystallizing compound (1) to form I is equal to 9. In another embodiment, the volume-to-weight ratio of ethanol/water mixture to compound (1) used for crystallizing compound (1) to form I is equal to 6.

In one embodiment, the cooling of step 3) can be achieved over various periods of time and various temperature frames. For example, the mixture can be cooled to a temperature of 3° C. to 5° C. for a period of about 6 hours, before being maintained at this temperature for about 12 hours. Alternatively, a quick cooling the mixture to 37° C. can be performed, followed by an isotherm for 3 h, then further cooling down to about 5° C. over 16 hours. Depending on the cooling parameters, various yields of recovery and purity can be achieved. One skilled in the art would be able to determine suitable conditions for cooling.

The crystals obtained at step 3) can be retrieved by filtration and dried under reduced pressure if needed.

The invention further relates to a crystalline form of (2S,5R)-5-(2-chlorophenyl)-1-(2'-methoxy-[1,1'-biphenyl]-4-carbonyl)pyrrolidine-2-carboxylic acid, obtainable by the process comprising the steps of:

1) dissolving (2S,5R)-5-(2-chlorophenyl)-1-(2'-methoxy-[1,1'-biphenyl]-4-carbonyl)pyrrolidine-2-carboxylic acid in an ethanol/water mixture, wherein the ethanol/water ratio is ranging from 100/0 to 5/95, at a temperature up to 80° C., preferably ranging from 40° C. to 60° C., more preferably from 45° C. to 55° C.;
2) if relevant, adding water in order to reach an ethanol/water ratio ranging from 95/5 to 5/95, wherein water is preferably heated at the same temperature as ethanol used in step 1); and
3) cooling the mixture, preferably to a temperature ranging from 0° C. to 10° C., more preferably from 3° C. to 5° C., and maintaining this temperature during a period of time suitable to recover the crystals.

The invention also relates to a process for preparing the crystalline form II of the invention, comprising crystallizing (2S,5R)-5-(2-chlorophenyl)-1-(2'-methoxy-[1,1'-biphenyl]-4-carbonyl)pyrrolidine-2-carboxylic acid from acetonitrile.

In one embodiment the process for preparing the crystalline form II comprises crystallizing (2S,5R)-5-(2-chlorophenyl)-1-(2'-methoxy-[1,1'-biphenyl]-4-carbonyl)pyrrolidine-2-carboxylic acid (compound (1)) from acetonitrile, at a temperature from room temperature up to 80° C., in a volume-to-weight ratio ranging from 2 to 3 volume of acetonitrile to compound (1) weight.

In one embodiment, the process for preparing the crystalline form II comprises the following steps:
1) dissolving (2S,5R)-5-(2-chlorophenyl)-1-(2'-methoxy-[1,1'-biphenyl]-4-carbonyl)pyrrolidine-2-carboxylic acid (compound (1)) in acetonitrile, at a temperature up to 80° C.; and
2) cooling the mixture of step 1), preferably to room temperature, and maintaining this temperature during a period of time suitable to recover crystalline form II.

In one embodiment, the volume-to-weight ratio of acetonitrile to compound (1) used in the process for preparing form II is ranging from 2 to 3, preferably from 2.2 to 2.3.

In one embodiment, the cooling of step 2) can be achieved over various periods of time and various temperature frames. For example, the mixture of step 1) can be cooled to room temperature, before being maintained at this temperature for about 1 hour. Depending on the cooling parameters, various yields of recovery and purity can be achieved. One skilled in the art would be able to determine suitable conditions for cooling.

The crystals obtained at step 2) can be retrieved by filtration and dried under reduced pressure in needed.

The invention further relates to a crystalline form of (2S,5R)-5-(2-chlorophenyl)-1-(2'-methoxy-[1,1'-biphenyl]-4-carbonyl)pyrrolidine-2-carboxylic acid, obtainable by the process comprising the steps of:
1) dissolving (2S,5R)-5-(2-chlorophenyl)-1-(2'-methoxy-[1,1'-biphenyl]-4-carbonyl)pyrrolidine-2-carboxylic acid (compound (1)) in acetonitrile, at a temperature up to 80° C.; and
2) cooling the mixture of step 1), preferably to room temperature, and maintaining this temperature during a period of time suitable to recover the crystals.

Seed crystals may be added to any crystallization mixture to promote crystallization.

Crystalline forms I or II can be prepared directly from the reaction medium of the final process for preparing compound (1). Alternatively, crystalline forms I or II can be obtained after one or more preliminary step of crystallization, followed by a re-crystallization pursuant to above described processes.

Due to their characteristics, above processes of preparation of crystalline form I or form II can be advantageously applied downstream of any synthetic process of compound (1) described in the prior art.

Especially, the processes of preparation of crystalline form I and form II can be applied downstream of the process of manufacturing compound (1) reported in WO2021/250174.

In one embodiment, it is thus provided a process of preparation of crystalline form I comprising:
a) a step of hydrochloride salt formation and epimer separation, consisting in crystallizing a mixture of epimers (6) and (6'):

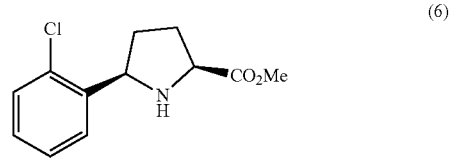

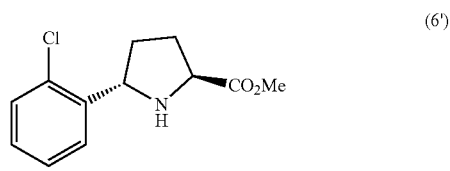

wherein the epimers ratio (6):(6') is at least 4:1, in presence of hydrochloric acid, in a solvent selected from an alcohol solvent (such as isopropyl alcohol, methanol, and mixtures thereof), isopropyl acetate, and mixtures thereof;

leading to of (2S,5R)-methyl 5-(2-chlorophenyl)pyrrolidine-2-carboxylate hydrochloride (6.HCl):

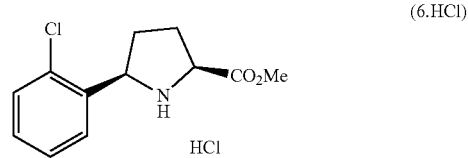 [SMILES: COC(=O)[C@@H]1CC[C@H](c2ccccc2Cl)N1 ; Cl]

b) forming methyl ester (9) from compound (6.HCl) obtained in step a),

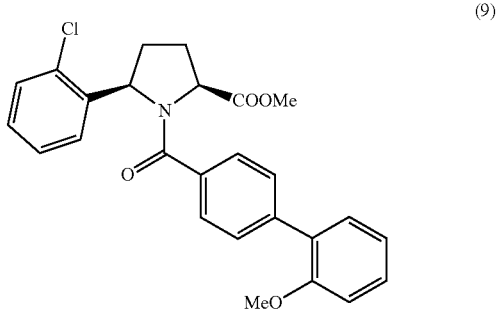 [SMILES: COC(=O)[C@@H]1CC[C@H](c2ccccc2Cl)N1C(=O)c1ccc(-c2ccccc2OC)cc1]

b1) by acylating compound (6.HCl) with compound (7):

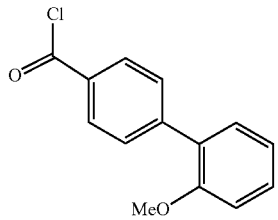

(7)

in presence of potassium carbonate, in a mixture of toluene and water as solvent, or b2) by coupling compound (6.HCl) with compound (8):

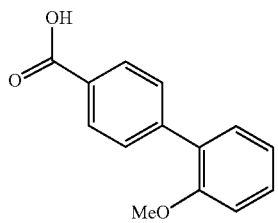

(8)

in presence of a base and an acid-activating agent;

c) saponifying methyl ester (9) in presence of sodium hydroxide and tetra-n-butylammonium bromide (TBAB) in a mixture of toluene and water as solvent, leading to acid compound (1); and d) performing the process of for preparing the crystalline form I of the invention as detailed above.

In one embodiment, an intermediate step of purification ci) can be performed between step c) and step d) in above process in order to further purify compound (1) before crystallization under form I.

In one embodiment, it is also provided a process of preparation of crystalline form II comprising:

steps a), b) and c) recited above; and d') performing the process of for preparing the crystalline form II of the invention as detailed above.

In one embodiment, an intermediate step of purification ci) can be performed between step c) and step d') in above process in order to further purify compound (1) before crystallization under form II.

Pharmaceutical Compositions

The present invention also provides pharmaceutical compositions comprising the crystalline form I and/or form II according to the invention, and at least one pharmaceutically acceptable carrier.

In one embodiment, the invention provides a pharmaceutical composition comprising crystalline form I according to the invention, and at least one pharmaceutically acceptable carrier. In another embodiment, the invention provides a pharmaceutical composition comprising crystalline form II according to the invention, and at least one pharmaceutically acceptable carrier. In another embodiment, the invention provides a pharmaceutical composition comprising a mixture of crystalline form I and crystalline form II according to the invention, and at least one pharmaceutically acceptable carrier.

In one embodiment, the pharmaceutical composition of the invention comprises the crystalline form I and/or form II, at least one pharmaceutically acceptable carrier, and optionally one or more further pharmaceutically active agents.

By means of non-limiting examples, the pharmaceutical composition of the invention may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such pharmaceutical preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use), which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc.. The compositions may also be formulated so as to provide rapid, sustained or delayed release of the active compound(s) contained therein.

In one embodiment, the pharmaceutical composition of the invention is in a form suitable for oral administration, preferably selected from tablets, pills, soft and hard gelatin capsules, powders, lozenges, sachets, cachets, elixirs, suspensions, emulsions, solutions, and syrups.

The pharmaceutical compositions of the invention are preferably in a unit dosage form, and may be suitably packaged, for example in a box, blister, vial, bottle, sachet, ampoule or in any other suitable single-dose or multi-dose holder or container (which may be properly labelled); optionally with one or more leaflets containing product information and/or instructions for use.

Generally, such unit dosages will contain between 0.05 and 1000 mg, and usually between 1 and 500 mg, of the crystalline form I and/or form II according to the invention, e.g. about 10, 25, 50, 100, 200, 300 or 400 mg per unit dosage.

Usually, depending on the condition to be prevented or treated and the route of administration, the crystalline form I and/or form II may usually be administered between 0.01 to 100 mg per kilogram, more often between 0.1 and 50 mg, such as between 1 and 25 mg, for example about 0.5, 1, 5, 10, 15, 20 or 25 mg, per kilogram body weight of the patient per day, which may be administered as a single daily dose, divided over one or more daily doses, or essentially continuously, e.g. using a drip infusion.

Medical Uses

Compound (1), (2S,5R)-5-(2-chlorophenyl)-1-(2'-methoxy-[1,1'-biphenyl]-4-carbonyl)pyrrolidine-2-carboxylic acid, is an agonists of FFAR2 and is useful for the treatment of diseases associated with or mediated by FFAR2, especially inflammatory diseases and cancers.

The invention thus provides the use of crystalline form I and/or form II for use as a medicament.

The invention also provides the use of crystalline form I and/or form II for the treatment of inflammation.

In one embodiment, the crystalline form I and/or form II is for use in the treatment of inflammation.

In one embodiment, the crystalline form I and/or form II is for use in the treatment of an inflammatory disease.

In one embodiment, the crystalline form I and/or form II is for use in delaying in a patient the onset of an inflammatory disease.

In one embodiment, the crystalline form I and/or form II is for use in the treatment of the diseases selected from the group consisting of rheumatoid arthritis; inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); immune-mediated colitis (IMC) (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute myelogenous leukemia; chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; autoimmune brain diseases such as encephalitis and encephalomyelitis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1) such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease.

In one embodiment, the crystalline form I and/or form II is for use in the treatment of the diseases selected from the group consisting of rheumatoid arthritis; inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute and chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1) such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease.

In one embodiment, the crystalline form I and/or form II is for use in the treatment of the diseases selected from the group consisting of inflammatory bowel disease (IBD), Crohn's disease, ulcerative colitis, colitis, collagenous colitis, lymphocytic colitis, immune-related enterocolitis (including as an adverse event in response to cancer therapy with checkpoint inhibitors such as inhibitors of CTLA-4, PD-1, PD-L1), immune-mediated colitis (IMC) (including as an adverse event in response to cancer therapy with checkpoint inhibitors such as inhibitors of CTLA-4, PD-1, PD-L1), pouchitis, Celiac disease, irritable bowel syndrome, gut dysbiosis, type 1 diabetes, multiple sclerosis, autoimmune brain diseases such as encephalitis and encephalomyelitis.

In one embodiment, the crystalline form I and/or form II is for use in the treatment of the diseases selected from the group consisting of inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.).

The invention also relates to a method for treating inflammation in a patient in need thereof, comprising administering to said patient a therapeutically effective amount of the crystalline form I and/or form II of the invention.

In one embodiment, the invention provides a method for treating an inflammatory disease in a patient in need thereof, comprising administering to said patient a therapeutically effective amount of the crystalline form I and/or form II of the invention.

In one embodiment, the invention provides a method for delaying in a patient in need thereof the onset of an inflammatory disease, comprising administering to said patient a therapeutically effective amount of the crystalline form I and/or form II of the invention.

In one embodiment, the invention provides a method for treating a disease selected from the group consisting of rheumatoid arthritis; inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); immune-mediated colitis (IMC) (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute myelogenous leukemia; chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; autoimmune brain diseases such as encephalitis and encephalomyelitis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1) such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease; in a patient in need thereof, comprising administering to said patient a therapeutically effective amount of the crystalline form I and/or form II of the invention.

In one embodiment, the invention provides a method for treating a disease selected from the group consisting of rheumatoid arthritis; inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute and chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1) such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease; in a patient in need thereof, comprising administering to said patient a therapeutically effective amount of the crystalline form I and/or form II of the invention.

In one embodiment, the invention provides a method for treating a disease selected from the group consisting of inflammatory bowel disease (IBD), Crohn's disease, ulcerative colitis, colitis, collagenous colitis, lymphocytic colitis, immune-related enterocolitis (including as an adverse event in response to cancer therapy with checkpoint inhibitors such as inhibitors of CTLA-4, PD-1, PD-L1), immune-mediated colitis (IMC) (including as an adverse event in response to cancer therapy with checkpoint inhibitors such as inhibitors of CTLA-4, PD-1, PD-L1), pouchitis, Celiac disease, irritable bowel syndrome, gut dysbiosis, type 1 diabetes, multiple sclerosis, autoimmune brain diseases such as encephalitis and encephalomyelitis; in a patient in need thereof, comprising administering to said patient a therapeutically effective amount of the crystalline form I and/or form II of the invention.

In one embodiment, the invention provides a method for treating a disease selected from the group consisting of inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); in a patient in need thereof, comprising administering to said patient a therapeutically effective amount of the crystalline form I and/or form II of the invention.

The invention also relates to the use of the crystalline form I and/or form II of the invention for the manufacture of a medicament for the treatment of inflammation.

In one embodiment, the invention provides the use of the crystalline form I and/or form II of the invention for the manufacture of a medicament for treating an inflammatory disease.

In one embodiment, the invention provides the use of the crystalline form I and/or form II of the invention for the manufacture of a medicament for delaying in a patient the onset of an inflammatory disease.

In one embodiment, the invention provides the use of the crystalline form I and/or form II of the invention for the manufacture of a medicament for the treatment of the diseases selected from the group consisting of rheumatoid arthritis; inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); immune-mediated colitis (IMC) (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute myelogenous leukemia; chronic myelogenous leukemia; pancreatic 3 cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; autoimmune brain diseases such as encephalitis and encephalomyelitis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1) such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease.

In one embodiment, the invention provides the use of the crystalline form I and/or form II of the invention for the manufacture of a medicament for the treatment of the diseases selected from the group consisting of rheumatoid arthritis; inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1); pouchitis; Celiac disease; irritable bowel syndrome; gut dysbiosis including antibiotic-induced dysbiosis leading to bacterial infection (e.g. *C. difficile* infection, pulmonary pneumococcal infection, etc.); Pagets disease; osteoporosis; multiple myeloma; uveitis; acute and chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis including hepatitis B virus infection; asthma; muscle degeneration; cachexia such as cachexia secondary to infection or malignancy, cachexia secondary to acquired immune deficiency syndrome; Reiter's syndrome; type I diabetes; bone resorption disease; graft vs. host reaction; ischemia reperfusion injury; brain trauma; multiple sclerosis; cerebral malaria; sepsis; septic shock; toxic shock syndrome; endotoxic shock; gram negative sepsis; fever and myalgias due to infection such as influenza; pyrosis; inflammatory conditions consequent to the release of anorectic gut hormones (e.g. PYY, GLP-1) such as the inflammatory conditions observed in hyperphagia-related disorders, obesity, type 2 diabetes etc.; microbiome-related neurological and mood disorders, including Autism spectrum disorder, schizophrenia, depression, Major Depressive Disorder, and neurodegenerative diseases characterized by neuroinflammation including Alzheimer's and Parkinson's disease.

In one embodiment, the invention provides the use of the crystalline form I and/or form II of the invention for the manufacture of a medicament for the treatment of the diseases selected from the group consisting of inflammatory bowel disease (IBD), Crohn's disease, ulcerative colitis, colitis, collagenous colitis, lymphocytic colitis, immune-related enterocolitis (including as an adverse event in response to cancer therapy with checkpoint inhibitors such as inhibitors of CTLA-4, PD-1, PD-L1), immune-mediated colitis (IMC) (including as an adverse event in response to cancer therapy with checkpoint inhibitors such as inhibitors of CTLA-4, PD-1, PD-L1), pouchitis, Celiac disease, irritable bowel syndrome, gut dysbiosis, type 1 diabetes, multiple sclerosis, autoimmune brain diseases such as encephalitis and encephalomyelitis.

In one embodiment, the invention provides the use of the crystalline form I and/or form II of the invention for the manufacture of a medicament for the treatment of the diseases selected from the group consisting of inflammatory bowel disease (IBD) including but not limited to Crohn's disease and ulcerative colitis; colitis; collagenous colitis; lymphocytic colitis; immune-related enterocolitis (including as an adverse event in response to cancer therapy with checkpoint inhibitors such as inhibitors of CTLA-4, PD-1, PD-L1), pouchitis; Celiac disease; irritable bowel syndrome; gut dysbiosis including antibiotic-induced dysbiosis leading to bacterial infection (e.g. *C. difficile* infection, pulmonary pneumococcal infection, etc.).

The invention also provides the use of crystalline form I and/or form II for the treatment of cancer.

In one embodiment, the crystalline form I and/or form II is for use in the treatment of cancer.

The invention also relates to a method for treating cancer in a patient in need thereof, comprising administering to said patient a therapeutically effective amount of the crystalline form I and/or form II of the invention.

The invention also relates to the use of the crystalline form I and/or form II of the invention for the manufacture of a medicament for the treatment of cancer.

In one embodiment, the crystalline form I and/or form II is for use in delaying in a patient the onset of cancer.

In one embodiment, the invention provides a method for delaying in a patient in need thereof the onset of cancer, comprising administering to said patient a therapeutically effective amount of the crystalline form I and/or form II of the invention.

In one embodiment, the invention provides the use of the crystalline form I and/or form II of the invention for the manufacture of a medicament for delaying in a patient the onset of cancer.

Non-limiting examples of cancers comprise lung cancer, non-small cell lung cancer, small cell lung cancer, breast cancer, prostate cancer, ovarian cancer, endometrial cancer, vaginal cancer, testicular cancer, cervical cancer, bladder cancer, head and neck cancer, kidney cancer, renal cell carcinoma, esophageal cancer, pancreatic cancer, brain cancer, thyroid cancer, gastrointestinal cancer, colorectal cancer, stomach cancer, colon cancer, liver cancer, leukemia, lymphoma, skin cancer, melanoma, multiple myeloma, glioma, glioblastoma, mesothelioma, retinoblastoma, sarcoma, Ewing's sarcoma, Kaposi's sarcoma, osteosarcoma, fibrosarcoma, bone cancer, and cardiac cancer.

In certain embodiments, the crystalline form I and/or form II is used in combination with an additional pharmaceutical agent. For example, the additional pharmaceutical agent may be a second anti-cancer therapy, such as chemotherapy, immunotherapy, cell therapy, surgery, transplantation, and/or any anti-cancer agent currently in clinical use or in clinical trials.

In the context of the present invention the term "combination" preferably means a combined occurrence of crystalline form I and/or form II and an additional pharmaceutical agent. Therefore, the combination may occur either as one composition, comprising all the components in one and the same mixture (e.g. a pharmaceutical composition), or may occur as a kit of parts, wherein the different components form different parts of such a kit of parts. The administration of the crystalline form I and/or form II and of the additional pharmaceutical agent may occur either simultaneously or timely staggered, with similar or different timing of administration (i.e. similar or different numbers of administration of each component), either at the same site of administration or at different sites of administration, under similar of different dosage forms.

EXAMPLES

The present invention is further illustrated by the following examples.

Example 1: Manufacturing of crystalline forms I and II

The starting material, (2S,5R)-5-(2-chlorophenyl)-1-(2'-methoxy-[1,1'-biphenyl]-4-carbonyl)pyrrolidine-2-carboxylic acid (herein referred to as compound (1)), was obtained as described in WO2021/250174.
Crystalline Form I
Crystallization of compound (1) under form I was achieved from a 70:30 ethanol:water mixture, at 6 volumes.
Compound (1) was dissolved at 48-52° C. in 3.7 volume of ethanol, filtered, and rinsed with 0.5 volume ethanol (heated to 48-52° C.).
1.8 volume of deionized water was heated to 48-52° C., filtered, and added to the ethanol filtrate. The mixture was cooled to 3-5° C. over a period of 6 hours and then kept at this temperature for 12 hours.
The wet product was filtered, sieved (as necessary), and dried at 40° C. It was identified as crystalline form I, as detailed hereafter.
Crystalline Form II
Compound (1) (3.57 g, 7.7 mmol) was solubilized in acetonitrile (8 ml) and stirred at 80° C. After 2-3 min, completed solubilization was obtained and crystallization began. The mixture was stirred at room temperature for 1 hour.
The crystals were filtered and dried under reduced pressure (10 mbar) for 20 h to afford 2.45 g of white crystals which were identified as crystalline form II, as detailed hereafter.

Example 2: X-Ray Powder Diffraction (XRPD)

The X-ray powder diffraction (XRPD) analyses were performed on a PANalytical X'Pert Pro diffractometer, in transmission mode (40 kV, 40 mA, Cu K$\alpha_1$ 1.5406 Å). The analyses were performed in the 2° to 500 range of 2θ values (continuous scanning mode, scanning rate 0.04 degrees/sec).
The XRPD pattern of crystalline form I is reported in FIG. 1. Selected diffraction peaks are shown in Table 1 provided above in the detailed description.

The XRPD pattern of crystalline form II is reported in FIG. 5. Selected diffraction peaks are shown in Table 2 provided above in the detailed description.

One skilled in the art will appreciate that an XRPD pattern may be obtained with a measurement error that is dependent upon the measurement conditions employed. Especially, it is known that intensities in a XRPD pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional XRPD pattern is typically about 5% or less, and such degree of measurement error should be taken into account as pertaining to the aforementioned diffraction angles.

Consequently, it is to be understood that the crystalline form I and form II of the instant invention are not limited to the crystal structure that provide XRPD pattern completely identical to the XRPD patterns depicted in FIG. 1 and FIG. 5. Any crystal structure that provides an XRPD pattern substantially identical to the one disclosed in FIG. 1 or FIG. 5 falls within the scope of the present invention. The ability to ascertain substantial identities of XRPD patterns is within the purview of one of ordinary skill in the art.

Example 3: Single Crystal X-Ray Analysis

A single crystal of crystalline form I was obtained and investigated by X-ray diffraction.
Data collection was carried out on a rigaku Ru200 rotating anode (Mo, λ=0.71073 Å). The X-rays were monochromated with a Zr-filter, and data were recorded on a MAR345 image plate. A 0.18×0.14×0.06 mm crystal was selected for the experiment and was mounted in a nylon loop on the diffractometer. During measurement, the crystal was cooled in gaseous nitrogen to 120 K. A total of 220 images were collected with phi increments of 3°. The MAR program was used to collect the diffraction data and the AUTOMAR suite was used to process the data. No absorption corrections were applied. The structure was solved by direct methods (SHELXS) and refined with (SHELXL-97) by full least squares refinement against F2. Non-hydrogen atoms were refined anisotropically and hydrogen atoms were placed on calculated positions and refined in riding mode on the parent atoms. The absolute configuration was calculated based on anomalous dispersion effects and the final Flack parameter was 0.07(12) and the Hooft parameter 0.08(3) for a Friedel pair coverage of 100%.

The crystalline form I crystallizes in an orthorhombic cell structure, the unit cell parameters equal to:
Cell dimensions:
a=11.51(2) A
b=13.95(3) A
c=15.14(3) A
α, β, γ=90°
Space group: $P2_12_12_1$
Molecules per unit cell: 4
Unit cell volume: 2430.9 (8) Å$^3$
Density (calculated): 1.19 g/cm$^3$
Mu(MoKa)[/mm]=0.186
F(000)=912

Example 4: Differential Scanning Calorimetry (DSC)

The differential scanning calorimetry (DSC) analyses were performed on a Mettler Toledo DSC3+ apparatus. The samples (few milligrams) were placed in a 40 μL aluminum sample pan and crimped with a punctured cover. The analyses were performed under nitrogen purge (50 mL/min) with a temperature scan between 20° C. and 300° C. at 10° C./min.

As shown in FIG. 2, the crystalline form I has a DSC thermogram which exhibits an endotherm with a peak temperature of about 183° C. and an onset temperature of about 180° C. Form I is a non-solvated crystalline form as evidence by its DSC analysis.

As shown in FIG. 6, the crystalline form II has a DSC thermogram which exhibits a first endothermal signal, with an onset at about 100° C., and a peak temperature of about 110° C., corresponding to the melting of the sample.

A recrystallization—melting phenomenon is then observed, with an exothermal signal with an onset at about 134° C., and a peak temperature of about 149° C. and an endothermal signal with an onset at about 179° C., and a peak temperature of about 181° C. Form II is a non-solvated crystalline form as evidence by its DSC analysis.

One of skill in the art will appreciate that in DSC measurement, there is a certain degree of variability in actual measured onset and peak temperatures, depending on rate of heating, crystal shape and purity, and other measurement parameters.

Consequently, it is to be understood that the crystalline form I and form II of the instant invention are not limited to the crystal structure that provide DSC thermogram completely identical to the DSC thermogram depicted in FIG. 2 and FIG. 6. Any crystal structure that provides a DSC thermogram substantially identical to the one disclosed in FIG. 2 or FIG. 6 falls within the scope of the present invention. The ability to ascertain substantial identities of DSC thermograms is within the purview of one of ordinary skill in the art.

Example 5: Thermal Gravimetric Analysis (TGA)

The thermal gravimetric analysis (TGA) experiments were performed on a Mettler Toledo TGA/DSC3+ apparatus. The samples (about 10-30 mg) were placed in a 100 μL aluminum sample pan and crimped with a punctured cover. The analyses were performed under nitrogen purge (50 mL/min) with a temperature scan between 25° C. and 300° C. at 10° C./min heating rate.

As shown in FIG. 3, the TGA analysis performed on crystalline form I does not highlight any significant weight loss below 220° C.: a weight loss of −0.14% is measured on the temperature range 10° C.-200° C. Above this temperature, the weight loss observed is likely due to the evaporation and/or degradation and this event is not over at the end of the analysis.

As shown in FIG. 7, the TGA analysis performed on crystalline form II does not highlight any significant weight loss below 220° C.: a weight loss of −0.2% is measured on the temperature range 10° C.-200° C. Above this temperature, the weight loss observed is likely due to the evaporation and/or degradation of the sample.

Example 6: Hygroscopicity Study—Dynamic Vapor Sorption (DVS)

The previously described solid forms of (2S,5R)-5-(2-chlorophenyl)-1-(2'-methoxy-[1,1'-biphenyl]-4-carbonyl) pyrrolidine-2-carboxylic acid, i.e. the amorphous free acid and the corresponding Na salt, both disclosed in WO2021/250174, are hygroscopic.

Especially, the amorphous free acid form displays a 8 wt % gain after only 14 h at 70-75% relative humidity at room temperature, and a 3 wt % gain at 40% relative humidity after 2 days.

The Na salt displays a 20 wt % gain after only 14 h at 70% relative humidity at 22° C., and a 7 wt % gain at 40% relative humidity after 14 h.

The determination of the hygroscopicity of crystalline forms I and II was thus critical.

It was evidenced that the Form I only displays a 0.09 wt % gain after 10 days at 80% relative humidity at 25° C.

The determination of the hygroscopicity of crystalline forms I and II was also evaluated by dynamic vapor sorption (DVS).

The analyses were performed on a Surface Measurements System DVS Intrinsic. The samples were placed in an open aluminum pan. The analyses were performed at 25° C. Relative humidity (RH) was scanned between 0% RH and 95% RH, with 10% RH steps (40-0-95-0-95). The stability criterion was a variation in mass lower than 0.002% on a 5 min. window, with a minimum step time of 10 min and a maximum of 100 min.

As shown in FIG. 4, the DVS analysis does not show any significant weight gain for crystalline form I when exposed to high relative humidity values. On the first desorption stage (40% RH to 0% RH), a weight loss of −0.1% is observed. On the first sorption stage (0% RH to 95% RH), a small water uptake is observed, mostly at high relative humidity values: at the end of the step at 70% RH, the weight gain is +0.1% and the maximum is reached at 95% RH with +0.7%. On the second desorption stage (95% RH to 0% RH), the sample loses all the water gained during the first sorption stage and reaches back the value observed at the end of the first desorption stage. The second sorption stage (0% RH to 95% RH) is similar to the first one.

Figure 8:
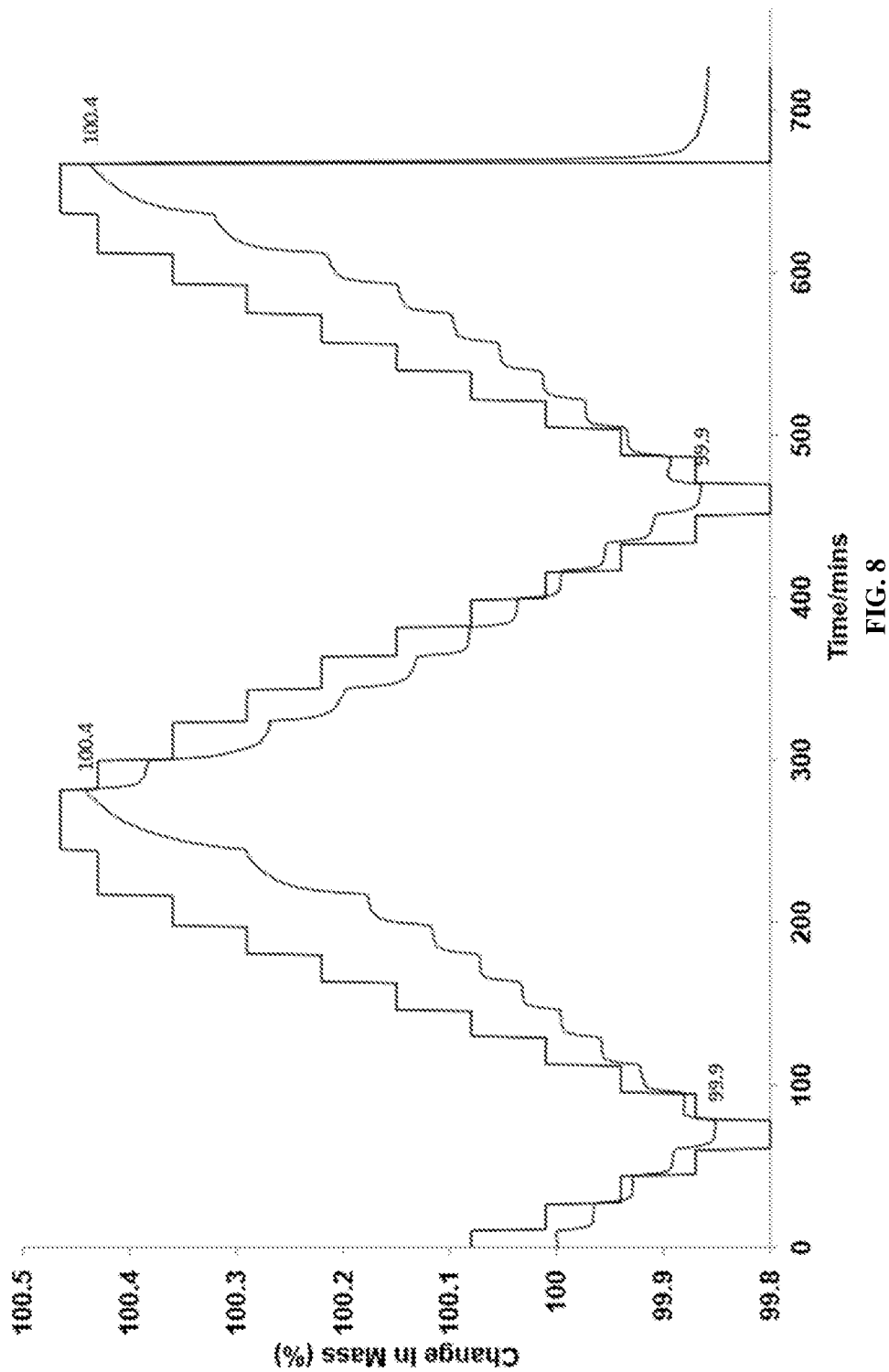
FIG. 8 is a DVS isotherm plot of the crystalline form II.

As shown in FIG. 8, the DVS analysis does not show any significant weight gain for crystalline form II when exposed to high relative humidity values. On the first desorption stage (40% RH to 0% RH), a weight loss of −0.1% is observed. On the first sorption stage (0% RH to 95% RH), a small water uptake is observed, mostly at high relative humidity values: at the end of the step at 70% RH, the weight gain is +0.1% and the maximum is reached at 95% RH with +0.4%. On the second desorption stage (95% RH to 0% RH), the sample loses all the water gained during the first sorption stage and reaches back the value observed at the end of the first desorption stage. The second sorption stage (0% RH to 95% RH) is similar to the first one.

At the end of the analyses, the samples were recovered and analyzed by X-ray diffraction. No phase change was detected: the diffractogram corresponds to the profile of each starting material.

Conclusion: Both crystalline forms I and II were evidenced to be non-hygroscopic, contrary to what was observed with the amorphous form and the Na salt of (2S,5R)-5-(2-chlorophenyl)-1-(2'-methoxy-[1,1'-biphenyl]-4-carbonyl)pyrrolidine-2-carboxylic acid.

Example 7: Stability Study

The relative stability of crystalline forms I and II was assessed by competitive slurry tests and cross seeding tests. The analyses evidenced that form I is more stable than form II.

Competitive Slurry Test in Isopropyl Alcohol

A competitive slurry test between form I and form II of compound (1) was carried out at 10° C., 20° C., 25° C., 30° C. and 40° C. in isopropyl alcohol.

Method. Suspensions of compound (1) under form II, in isopropyl alcohol, were first prepared and equilibrated for 30 min at each of the temperatures to be studied. About 800 μL of the saturated solutions were then sampled, filtered through a 0.2 μm HPTFE filter, and added into a vial containing 50 mg of form I and 50 mg of form II, equipped with a magnetic rod. After 10 seconds, a first sample of the solid phase is taken and analyzed by XRPD to identify the solid phase(s) present. Additional sampling are also performed until only 1 solid phase remains.

Results. The results of the XRPD analyses for each temperature were compared to the diffraction profiles of form I and form II. Form II is not visible anymore in the suspensions since the first sampling (.e. after 10 seconds). The results have shown that form I is more stable than form II in the tested range of temperature in isopropyl alcohol.

Competitive Slurry Test in n-Heptane

A competitive slurry test between form I and form II of compound (1) was carried out at 10° C., 20° C., 25° C., 30° C. and 40° C. in n-heptane.

Method. About 1 mL of n-heptane was added into vials containing 40 mg of form I and 40 mg of form II, equipped with a magnetic rod. After 10 seconds, a first sample of the solid phase is taken and analyzed by XRPD to identify the solid phase(s) present. Additional sampling are also performed until only 1 solid phase remains.

Results. The results of the XRPD analyses for each temperature were compared to the diffraction profiles of form I and form II. The results have shown the conversion of form II into form I over the whole temperature range investigated in n-heptane.

Cross-Seeding Tests

Cross-seeding tests were carried out in water and n-heptane.

Method. Saturated solutions of form II were prepared at 25° C. in water and in n-heptane. The suspensions were then seeded with form I after 45 minutes, and kept under stirring at 25° C. The solid phases in suspensions were then periodically controlled by XRPD.

Results. The results of the cross-seeding tests in water and n-heptane show the greater stability of form I vs. form II at 25° C.

The invention claimed is:

1. A crystalline form of (2S,5R)-5-(2-chlorophenyl)-1-(2'-methoxy-[1,1'-biphenyl]-4-carbonyl)pyrrolidine-2-carboxylic acid, of form I or form II, wherein:
   form I is characterized by an X-ray powder diffraction (XRPD) pattern comprising peaks at 2θ angle values of 13.5°, 14.0°, 14.8°, 16.0° and 18.0°; and
   form II is characterized by an XRPD pattern comprising peaks at 2θ angle values of 10.8°, 12.1°, 12.4° and 22.3°.

2. The crystalline form I according to claim 1, having an XRPD pattern comprising peaks at 2θ angle values of 7.2°, 12.8°, 13.5°, 14.0°, 14.5°, 14.8°, 16.0°, 16.7°, 17.4°, 18.0°, 18.9°, 19.9°, 20.4°, and 23.2°.

3. The crystalline form I according to claim 1, having an XRPD pattern substantially as shown in FIG. 1.

4. The crystalline form I according to claim 1, having a differential scanning calorimetry (DSC) thermogram which exhibits an endotherm with a peak temperature of about 183° C. and an onset temperature of about 180° C.

5. The crystalline form I according to claim 1, having unit cell parameters equal to:
   Cell dimensions:
   a=11.51(2) Å
   b=13.95(3) Å
   c=15.14(3) Å
   α, β, γ=90°
   Space group: $P2_12_12_1$
   Molecules per unit cell: 4
   Unit cell volume: 2430.9 (8) Å$^3$
   Density (calculated): 1.19 g/cm$^3$.

6. The crystalline form II according to claim 1, having an XRPD pattern comprising peaks at 2θ angle values of 10.8°, 12.1°, 12.4°, 15.3°, 16.2°, 18.5°, 19.5°, 20.7°, 21.5° and 22.3°.

7. The crystalline form II according to claim 1, having an XRPD pattern substantially as shown in FIG. 5.

8. The crystalline form II according to claim 1, having a DSC thermogram which exhibits a first endotherm, with a peak temperature of about 110° C. and an onset at about 100° C., an exotherm with a peak temperature of about 149° C. and an onset at about 134° C., and a second an endotherm with a peak temperature of about 181° C. and an onset at about 179° C.

9. A pharmaceutical composition comprising a crystalline form according to claim 1, and at least one pharmaceutically acceptable carrier.

10. A method for treating inflammation associated with a disease selected from rheumatoid arthritis; inflammatory bowel disease (IBD), Crohn's disease, ulcerative colitis; colitis; collagenous colitis; lymphocytic colitis; immune-related enterocolitis; immune-mediated colitis (IMC); pouchitis; Celiac disease; irritable bowel syndrome; gut dysbiosis; Pagets disease; osteoporosis; multiple myeloma; uveitis; acute myelogenous leukemia, chronic myelogenous leukemia; pancreatic R cell destruction; rheumatoid spondylitis; osteoarthritis; gouty arthritis and other arthritis conditions; gout; adult respiratory distress syndrome (ARDS); chronic pulmonary inflammatory diseases; silicosis; pulmonary sarcoidosis; psoriasis; rhinitis; anaphylaxis; contact dermatitis; pancreatitis; allergy; hepatitis; asthma; cachexia; Reiter's syndrome; type I diabetes; graft vs. host reaction; ischemia reperfusion injury; multiple sclerosis; autoimmune brain diseases, encephalitis, encephalomyelitis; sepsis; septic shock; toxic shock syndrome; endotoxic shock; gram negative sepsis; fever and myalgias due to infection; inflammatory conditions consequent to the release of anorectic gut hormones; and neurodegenerative diseases characterized by neuroinflammation, in a patient in need thereof comprising administering to said patient a therapeutically effective amount of the crystalline form according to claim 1.

11. The method according to claim 10, wherein the disease is selected from inflammatory bowel disease (IBD), Crohn's disease, ulcerative colitis, colitis, collagenous colitis, lymphocytic colitis, immune-related enterocolitis, immune-mediated colitis (IMC), pouchitis, Celiac disease, irritable bowel syndrome, gut dysbiosis, type 1 diabetes, multiple sclerosis, autoimmune brain diseases, encephalitis, and encephalomyelitis.

12. The method according to claim 10, wherein the immune-related enterocolitis is an immune-related enterocolitis occurring as an adverse event in response to cancer therapy with checkpoint inhibitors; and the immune-mediated colitis (IMC) is an immune-mediated colitis occurring as an adverse event in response to cancer therapy with checkpoint inhibitors.

13. The method according to claim 12, wherein the checkpoint inhibitors are inhibitors of CTLA-4, PD-1, and/or PD-L1.

14. The method according to claim 10, wherein the neurodegenerative diseases characterized by neuroinflammation are selected from Alzheimer's and Parkinson's disease.

15. A method of agonizing FFAR2 in a subject in need thereof, comprising administering an effective amount of the crystalline form according to claim 1 to said subject.

* * * * *